United States Patent [19]

Huybrechts

[11] Patent Number: 5,021,607

[45] Date of Patent: Jun. 4, 1991

[54] OXIDATION OF SATURATED HYDROCARBON CHAINS

[75] Inventor: Diana R. C. Huybrechts, Turnhout, Belgium

[73] Assignee: Exxon Chemical Patents Inc., Linden, N.J.

[21] Appl. No.: 536,679

[22] PCT Filed: Nov. 11, 1989

[86] PCT No.: PCT/GB89/01328

§ 371 Date: Sep. 10, 1990

§ 102(e) Date: Sep. 10, 1990

[87] PCT Pub. No.: WO90/05126

PCT Pub. Date: May 17, 1990

[30] Foreign Application Priority Data

Nov. 8, 1988 [BE] Belgium ............................. 08801275

[51] Int. Cl.$^5$ ............................................. C07C 45/28
[52] U.S. Cl. .................................... 568/311; 568/342; 568/385; 568/815; 568/836; 568/910

[58] Field of Search .............. 568/311, 385, 342, 815, 568/836, 910

[56] References Cited

U.S. PATENT DOCUMENTS

| | | | |
|---|---|---|---|
| 2,808,442 | 10/1957 | Smith et al. .......................... | 568/385 |
| 4,476,327 | 10/1984 | Neri et al. ............................ | 568/385 |
| 4,480,135 | 10/1984 | Esposito et al. ..................... | 568/385 |
| 4,824,976 | 4/1989 | Clerici et al. ....................... | 549/531 |
| 4,943,667 | 7/1990 | Hoelderich et al. ................ | 568/815 |

FOREIGN PATENT DOCUMENTS 0190609 8/1986 European Pat. Off. ............ 549/531

Primary Examiner—James H. Reamer
Attorney, Agent, or Firm—J. J. Mahon

[57] ABSTRACT

Saturated hydrocarbon chains are oxidized using a titanium containing silicalite catalyst having an infra red absorption band around 950 cm$^{-1}$ preferably in solutions, the chains may be alkanes or alkyl groups of alkyl cyclic compounds.

17 Claims, No Drawings

OXIDATION OF SATURATED HYDROCARBON CHAINS

The present invention relates to the oxidation of saturated hydrocarbon chains and in particular to the use of a certain catalyst system which has been found to enable the selective oxidation of aliphatic compounds and alkyl aromatic compounds.

Saturated organic compounds are particularly difficult to oxidise and despite attempts to develop methods and techniques for their controlled or selective oxidation techniques using mild conditions with relatively high yields are only known for the conversion of butane via butenes into maleic anhydride, furthermore the known processes use homogenous and sometimes hazardous catalysts requiring complex separation techniques. An example of such processes are given in Catalysis Today Vol I Nos 5 of October 1987 relative to the selective catalytic oxidation of butane to maleic anhydride involving dehydrogenation and oxidation of the resulting intermediate olefine, the article in Tetrahedron Vol 31 pages 777-784 concerning the oxidation of cyclohexane with molecular oxygen and the article in the Journal of the CHEM SOC CHERM COMMUN 1987 page 1487 and Journal of Molecular Catalysis 44 (1988) pages 73-83. The direct oxidation of saturates to introduce functional groups such as ketones and alcohols using a heterogeneous catalyst system would be extremely attractive.

Surprisingly we have now found that catalysts proposed for the epoxydation of olefins, the hydroxylation of aromatics and the oxidation of alcohols to ketones and aldehydes, as described in US-A-4,410,501; EP-A-200200, EP-B-100119, EP-A-196109, Ep-A-100118 and DE-A-3135559 can be used for the controlled oxidation of saturates under mild conditions enabling direct formation of alcohols and ketones without acid formation. In particular we have found that a synthetic silicon zeolite containing titanium atoms is able to cause saturated hydrocarbon groups and hydrogen peroxide or organic peroxides to react in a heterogeneous catalytic reaction to yield selectively alcohols and ketones.

These catalysts are based on crystalline synthetic material comprisiing silicon and titanium oxides and are characterized by an Infra red absorption band at around 950 cm$^{-1}$. They are typically of the general formula:

$$xTiO_2(1-x)SiO_2$$

where x is from 0.0001 to 0.04.

They are typically prepared from a mixture containing a source of silicon oxide, a source of titanium oxide, a nitrogenated organic base and water as described in United Kingdom Patent 2071071 which is concerned with the catalysts themselves or by the dealumination of ZSM-5 and reaction with titanium tetrachloride vapour as described by B. Kraushaar and J.H.C. Van Hoof in Catalysis Letters 1 (1988) pages 81-84. The catalysts may contain small amounts of other metals such as aluminium, gallium and iron (as described in European Patent Application 0226258).

U.S. Pat. No. 4824976 relates to the use of these types of catalysts for the epoxidation of olefines with $H_2O_2$ and in this patent X may be in the range from about 0.0001 to about 0.04. United Kingdom Patents 2083816 and 2116974 relate to the use of similar catalysts for the introduction of hydroxy groups into aromatic substrates by oxidation with $H_2O_2$. These patents are incorporated herein by reference for their descriptions of the Infrared and x ray diffraction analyses of the catalysts, as stated the band intensity at approximately 950 cm$^{-1}$ increases as the quantity of titanium present increases.

The invention therefore provides the use for the oxidation of saturated organic groups of a titanium containing silicalite catalyst having an infra red absorption band around 950 cm$^{-1}$.

Typically the catalyst is of the general formula $$xTiO_2(1-x)SiO_2$$

where x is 0.0001 to 0.04.

These catalysts may be typically prepared by:
i) heating a reaction mixture comprising:
a) a silicon oxide source ($SiO_2$),
b) a titanium oxide source ($TiO_2$),
c) optionally an alkali metal source,
d) a nitrogen containing organic base, and
e) water,
ii) separating the formed crystals from the reaction mixture and
iii) calcining the separated crystals to form the catalyst.

The catalyst may be agglomerated to form crystal clusters which are also active and readily recovered after the oxidation reaction.

The invention further provides a process for the oxidation of saturated organic groups by the treatment of the compound containing the saturated organic group with an oxidising agent in the presence of a titanium containing silicalite (catalyst having an infra red absorption band around 950 cm$^{-1}$.

Typically the catalyst is of the general formula:

$$xTiO_2(1-x)SiO_2$$

where x is 0.0001 to 0.04.

In the preferred process the oxidising agent is hydrogen peroxide or an organic peroxide and the compound containing the saturated organic group is liquid or in the dense phase at the conditions used for the reaction. It is also preferred that the reaction is carried out in the presence of a solvent.

The catalyst used in this invention is preferably prepared from a reaction mixture consisting of sources of silicon oxide, titanium oxide and possibly an alkaline oxide, a nitrogen containing organic base and water, the composition in terms of the molar reagent ratios being as heretofore defined.

The silicon oxide source can be a tetraalkylorthosilicate, preferably tetraethylorthosilicate, or simply a silicate in colloidal form, or again a silicate of an alkaline metal, preferably Na or K.

The titanium oxide source is a hydrolysable titanium compound preferably chosen from $TiOCl_4$, $TiOCl_2$ and Ti(alkoxy)$_4$, preferably Ti($OC_2H_5$)$_4$.

The organic base is tetraalkylammonium hydroxide, and in particular tetrapropylammonium hydroxide.

In the preferred method to produce the catalyst the mixture of these reactants is subjected to hydrothermal treatment in an autoclave at a temperature of between 130° and 200° C. under its own developed pressure, for a time of 1-30 preferably 6 to 30 days until the crystals of the catalyst precursor are formed. These are separated from the mother solution, carefully washed with water and dried. When in the anhydrous state they have the following composition:

$$xTiO_2.(1-x)SiO_2.0.04(RN^+)_2O.$$

The precursor crystals are then heated for between 1 and 72 hours in air at 550° C. to eliminate the nitrogenated organic base. The mixture is preferably heated in an autoclave at a temperature of 130°–200° C., preferably about 175° C., during a time period of one hour to 30 days, preferably about 10 days. The formed crystals are separated from the mother-liquor, are washed with water, dried and finally calcined. Said calcination may be realized at a temperature of 200–600, preferably 550° C., during about 20 hours. The final catalyst has the following composition:

$$xTiO_2.(1-x)SiO_2$$

where x is as heretofore defined.

The preferred molar ratio (MR) of the different reactants with regard to the silicon oxide source ($SiO_2$) are mentioned in the following table:

|  | MR | MR (preferably) |
|---|---|---|
| $TiO_2/SiO_2$ | 0.005–0.5 | 0.20 |
| $H_2O/SiO_2$ | 20–200 | 100 |
| $RN^+/SiO_2$ | 0.1–2.0 | 0.89 |

The catalyst may also contain alkali metal cations $M^+$ where M is sodium or potassium and in this situation it is preferred that the molar ratio of $M^+:SiO_2$ is in the range 0.001 to 0.5.

It is possible to oxidise saturated aliphatic compounds including aliphatic substituents of aliphatic/aromatic compounds by the process of the invention. The saturated groups which may be oxidised by the process of this invention include long or short, branched or linear alkanes containing 3 or more, preferably 3 to 18, more preferably 3 to 12 carbon atoms, cyclic alkanes and mono- and poly- alkyl aromatics in which at least one of the alkyl groups contain at least two preferably at least three, more preferably 3 to 18, most preferably 3 to 12 carbon atoms and mono- and poly- alkyl cyclic alkanes. We have surprisingly found that by the selection of appropriate conditions the saturated groups may be oxidised with high selectivity to alcohols and ketones under relatively mild conditions. One particularly useful application is in the oxidation of linear and branched paraffins to secondary alcohols and ketones The process is especially useful in the lower carbon number range to enable use of low-cost propane and butane feedstock in the manufacture of isopropanol alcohol, acetone, secondary butyl alcohol and methyl ethyl ketone. The aliphatic substituent may be a part of a totally aliphatic compound, an aryl compound (alkylaromatic) or an alkylnaphthene compound. Furthermore, said compound may contain other functional groups which have electron-repulsive properties and which, accordingly, are not reactive.

The reactivity sequence for the aliphatic compounds slows down from tertiary to secondary and to primary compounds.

The oxidising agents used in the reaction may be organic peroxides, ozone or hydrogen peroxide, aqueous hydrogen peroxide being preferred. The aqueous solution contains from 10–100, preferably 10 to 70 wt% hydrogen peroxide for example diluted hydrogen peroxide (40% by weight in water). It is also preferred that a polar solvent be present for example acetone or methanol, this will to increase the solubility of the organic compound in the $H_2O_2$ aqueous phase when aqueous hydrogen peroxide is used.

Particular advantages of the present invention are that the process uses mild temperature and pressure conditions and the conversion and yield are high and byproduct formation is small. In particular the conversion of hydrogen peroxide is high. The optimum reaction temperature is between 50 and 150° C., preferably about 100° C. The pressure should be such that all materials are in the liquid or dense phase.

The reaction can be carried out at room temperature but higher reaction rates may be involved at higher temperatures, for example under reflux conditions. Though increase of the pressure either due to the autogeneous pressure created by the heated reactants or by use of a pressurised reactor still higher temperatures can be reached Use of higher pressures in the range of 1 to 100 bars ($10^5$ to $10^7$ Pa) can increase the conversion and selectivity of the reaction The oxidation reaction can be carried out under batch conditions or in a fixed bed, and the use of the heterogeneous catalyst enables a continuous reaction in a monophase or biphase system. The catalyst is stable under the reaction conditions, and can be totally recovered and reused.

The process of the present invention is preferably carried out in the presence of a solvent Choice of solvent is important since it should dissolve the organic phase and the aqueous phase which is generally present due to the use of aqueous hydrogen peroxide as the oxidising agent. Polar compounds are preferred and examples of preferred solvents are alcohols, ketones, ethers, glycols and acids, with a number of carbon atoms which is not too high, preferably less than or equal to 6. Methanol or tertiary butanol is the most preferred of the alcohols, acetone the most preferred of the ketones, and acetic or propionic acid the most preferred acid. The amount of solvent is important and can influence the reaction product and the conversion, the choice of solvent and the amount depending on the material to be oxidised for example we have found that when oxidising normal hexane with aqueous hydrogen peroxide yields are improved when the ratio of acetone to hexane is in the range 1:1 to 4:1. The solvent improves the miscibility of the hydrocarbon phase and the aqueous phase which is generally present due to the use of aqueous hydrogen peroxide as the oxidising agent. The invention will be described with further details including a preparation of the catalyst and several examples of oxidation reactions.

Preparation of the catalyst 15g of tetraethylorthotitanate (available from Aldrich Chemical Company) are slowly dropped under stirring into 250 ml of distilled water, so that hydrolysis started. The white suspension produced was cooled to 2° C., whereafter 180 ml of a 30% by weight solution of hydrogen peroxide in water were added whilst cooling at 2° C. The mixture was stirred at this low temperature during 2 hours. Thereafter, 250 ml of a 25% by weight solution in water of tetrapropylammonium hydroxide (put on the market by Alfa as a 40% by weight solution containing sodium ions as impurity) are added, so as to form a clear orange solution After one hour, 50 g of a 40% by weight colloidal silica solution (Ludox Type SA 40) are added and the mixture was leaved at room temperature during the night. Finally, the whole was heated to 70°–80° C. for 6–7 hours under stirring. The yellow solution was then transferred into an autoclave and maintained at 175° C. during a time period of 10 days. The autoclave was thereafter cooled to room temperature and the formed crystals were separated by filtration of the mother-liquor, washed with distilled water and centrifuged. The product was thereafter dried and calcined at 550° C. in air for 20 hours.

EXAMPLES 1 to 4

Oxidation

The catalyst so prepared was used in the oxidation of the compounds set out in table 1.

Oxidation was carried out as follows. 15 ml of the compound listed in table 1, 16 ml of hydrogen peroxide (a 30% by weight solution in water), 30 ml of acetone and 1g of catalyst prepared according to example 1, were introduced in a 130 ml autoclave and thereafter stirred at 100° C. during 3 hours. The autoclave was then rapidly cooled to room temperature and its content was analysed through gas-chromatography and gas-chromatography/mass spectroscopy.

The results of the oxidation of several compounds are given in table 1.

TABLE 1

| Compound | Conversion | Selectivity | |
|---|---|---|---|
| n-hexane[a] | 80% | 3-hexanone | 24% |
| | | 2-hexanone | 51% |
| | | 3-hexanol | 18% |
| | | 2-hexanol | 5% |
| 2-methylpentane[b] | 69% | 2-methyl-2-pentanol | 52% |
| | | 4-methyl-2-pentanol | 22% |
| | | 4-methyl-2-pentanone | 9% |
| | | 2-methyl-3-pentanol | 7% |
| | | 2-methyl-3-pentanone | 4% |
| n-decane[b] | 84% | 2-decanone | 52% |
| | | 3-decanone | 20% |
| | | 3-decanol | 12% |
| | | 4-decanone | 11% |
| n-propylbenzene[b] | 4% | 1-phenyl-1-propanol | 37% |
| | | 1-phenyl-1-propanone | 27% |
| | | 1-phenyl-2-propanol | 5% |
| | | 1-phenyl-2-propanone | 5% |

[a]homogenous liquid phase at the end of the reaction
[b]phase-separation between an aqueous and organic phase at the end of the reaction, the conversion and the selectivity are determined for the aqueous phase, the conversion being the percentage of oxidised products to starting material present in the particular phase at the end of the reaction The table shows that, among others, the conversion can depend on the effective kinetic diameter of the aliphatic group to be oxidised.

EXAMPLE 5

The effect of varying the amount of acetone solvent used in the oxidation of n-hexane was determined in a series of reactions carried out in a stirred 300 ml PARR reactor using 500 mg of the catalyst used in the previous Examples, 15 ml of n-hexane, 21 ml of a 35% aqueous solution of hydrogen peroxide. The reaction mixture was heated to 100° C. for 2 hours, the autogeneous pressure generated in the reactor was 7 bars ($-7 \times 10^5$Pa).

The results are set out in Table 2.

TABLE 2

| ml acetone | Conversion C$_6$ % | Yield based on H$_2$O$_2$ % | SELECTIVITY | | | | YIELD | | | |
|---|---|---|---|---|---|---|---|---|---|---|
| | | | 3 hexanone % | 2 hexanone % | 2 hexanol % | 3 hexanol % | % 3 hexanone | % 2 hexanone | % 3 hexanol | % 2 hexanol |
| 0.00 | 0.70 | 0.70 | 48.85 | 51.15 | 0.00 | 0.00 | 0.34 | 0.36 | 0.00 | 0.00 |
| 10.00 | 19.33 | 17.30 | 33.86 | 45.23 | 5.44 | 15.37 | 6.55 | 8.74 | 2.97 | 1.05 |
| 20.00 | 53.42 | 48.95 | 30.72 | 52.61 | 3.54 | 13.06 | 16.41 | 28.10 | 6.98 | 1.89 |
| 30.00 | 51.52 | 46.11 | 25.80 | 53.29 | 4.04 | 16.78 | 13.29 | 27.46 | 8.65 | 2.08 |
| 45.00 | 48.74 | 42.04 | 23.13 | 49.50 | 5.91 | 21.34 | 11.27 | 24.13 | 10.40 | 2.88 |
| 60.00 | 40.37 | 31.40 | 17.25 | 38.56 | 12.36 | 31.57 | 6.96 | 15.57 | 12.74 | 4.99 |
| 90.00 | 25.37 | 17.84 | 13.16 | 27.94 | 20.33 | 38.16 | 3.34 | 7.09 | 9.68 | 5.16 |

EXAMPLE 6

310 mmoles of the saturated alkanes listed in Table 3 were oxidised in a stirred 300 ml PARR reactor using 210 mmol of hydrogen peroxide and 400 mg of the titanium silicalite catalyst used in the previous Examples with 60 ml of acetone as solvent. The reaction was at 100° C. for a period of 3 hours and generated an autogeneous pressure of 7 bars ($7 \times 10^5$Pa).

In all instances the hydrogen peroxide conversions were higher than 90% and the products obtained and their selectivity are given in Table 3.

TABLE 3

| Saturated Alkane | Product | Selectivity |
|---|---|---|
| n-pentane | 2-pentanol | 38% |
| | 3-pentanol | 20% |
| | 2-pentanone | 30% |
| | 3-pentanone | 12% |
| n-hexane | 2-hexanol | 14% |
| | 3-hexanol | 25% |
| | 2-hexanone | 39% |
| | 3-hexanone | 22% |
| n-octane | 2-octanol | 24% |
| | 3-octanol | 31% |
| | 4-octanol | 27% |
| | 2-octanone | 11% |
| | 3-octanone | 4% |
| | 4-octanone | 3% |
| n-decane | 2-decanol | 18% |
| | 3-decanol | 22% |
| | 4-decanol and 5-decanol | 43% |
| | 2-decanone | 10% |
| | 3-decanone | 3% |
| | 4-decanone and 5-decanone | 4% |
| 2-methylpentane | 2-methyl, 2-pentanol | 42% |
| | 4-methyl, 2-pentanol | 24% |
| | 2-methyl, 3-pentanol | 8% |
| | 2-methyl, 2-pentanone | 19% |
| | 2-methyl, 3-pentanone | 7% |
| 3-methylpentane | 3-methyl, 3-pentanol | 56% |
| | 3-methyl, 2-pentanol | 27% |
| | 3-methyl, 2-pentanone | 17% |
| 2,2-dimethylbutane | 3,3-dimethyl, 2-butanol | 93% |
| | 3,3-dimethyl, 2-butanone | 7% |

EXAMPLE 7

115 mmoles of cyclohexane were oxidised in a stirred 300 ml PARR reactor with 230 millimoles of hydrogen peroxide over 14 hours at 100° C. using 45 ml of acetone and 1 gram of the catalyst used in the previous Examples. A product mixture containing 39 wt% cyclohexanol and 61 wt% cyclohexanone was obtained. The conversion of cyclohexane was 21% and that of hydrogen peroxide over 90%.

I claim:

1. The use for the oxidation of saturated hydrocarbon chains a titanium containing silicalite catalyst having an infra red absorption band around 950 cm$^{-1}$.

2. The use according to claim 1 in which the catalyst is of the general formula $$xTiO_2(1-x)SiO_2$$

where x is 0.0001 to 0.04.

3. The use according to claim 1 or claim 2 in which the saturated hydrocarbon chain is an alkane containing from 2 to 18 carbon atoms.

4. The use according to any one of the preceding claims in which the saturated hydrocarbon chain is an alkyl group containing at least two carbon atoms attached to a ring structure.

5. The use according to claim 4 in which the alkyl group contains at least three carbon atoms.

6. The use according to claim 4 or claim 5 in which the ring structure is aromatic.

7. A process for the oxidation of saturated hydrocarbon chains by the treatment of the compound containing the saturated organic group with an oxidising agent in the presence of a titanium containing silicalite catalyst having an infra red absorption band around 950 cm$^{-1}$.

8. A process according to claim 7 in which the catalyst is of the general formula:

$$xTiO_2(1-x)SiO_2$$

where x is 0.0001 to 0.04.

9. A process according to claim 7 or claim 8 in which the oxidising agent is hydrogen peroxide or an organic peroxide.

10. A process according to any of claims 7 to 9 in which the compound containing the saturated organic group is liquid or in the dense phase at the conditions used for the reaction.

11. A process according to any of claims 7 to 10 in which the saturated hydrocarbon chain is an alkane containing from 2 to 18 carbon atoms.

12. A process according to any of claims 7 to 10 in which the saturated hydrocarbon chain is a alkyl group containing at least two carbon atoms attached to a ring structure.

13. A process according to claim 12 in which the alkyl group contains at least 3 carbon atoms.

14. A process according to any of claims 7 to 13 in which the reaction is carried out in the presence of a solvent.

15. A process according to any of claims 7 to 14 in which the oxidising agent is aqueous hydrogen peroxide.

16. A process according to any of claims 7 to 15 in which the solvent is a polar solvent.

17. A process according to any of claims 7 to 16 carried out at a temperature between 50° and 150° C.

* * * * *